(12) United States Patent
Ritchey et al.

(10) Patent No.: US 8,628,531 B2
(45) Date of Patent: Jan. 14, 2014

(54) ASSEMBLIES FOR THE REDUCTION OF A FRACTURE

(75) Inventors: Nicholas S. Ritchey, Collierville, TN (US); Nathaniel Kelley Grusin, Germantown, TN (US); Gene Edward Austin, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 878 days.

(21) Appl. No.: 12/162,172

(22) PCT Filed: Jan. 26, 2007

(86) PCT No.: PCT/US2007/002257
§ 371 (c)(1),
(2), (4) Date: Jul. 25, 2008

(87) PCT Pub. No.: WO2007/089637
PCT Pub. Date: Aug. 9, 2007

(65) Prior Publication Data
US 2009/0048598 A1    Feb. 19, 2009

Related U.S. Application Data

(60) Provisional application No. 60/762,988, filed on Jan. 27, 2006.

(51) Int. Cl.
*A61B 17/56* (2006.01)
*A61B 17/58* (2006.01)
*A61F 2/30* (2006.01)

(52) U.S. Cl.
USPC .............................................. 606/62; 606/282

(58) Field of Classification Search
USPC .................. 606/53–60, 62–68, 87, 96–100, 606/104–105, 280–282
See application file for complete search history.

(56) References Cited

U.S. PATENT DOCUMENTS

| 4,519,100 A | 5/1985 | Wills et al. |
| 4,846,162 A | 7/1989 | Moehring |

(Continued)

FOREIGN PATENT DOCUMENTS

| DE | 8533134 | 5/1986 |
| DE | 8533134 U1 | 5/1986 |

(Continued)

OTHER PUBLICATIONS

International Search Report; PCT/US2007/002257; Nov. 12, 2007; 5 pages.

(Continued)

*Primary Examiner* — Eduardo C Robert
*Assistant Examiner* — Michelle C Eckman
(74) *Attorney, Agent, or Firm* — Krieg DeVault LLP

(57) ABSTRACT

A controlled removable fracture-reducing assembly (10) for reducing a bone fracture. According to one embodiment of the present invention, a controlled removable fracture reducing assembly (10) includes an implant (12), a reducer (14), a buttress (16), and a locking device (18) that engage a proximal bone fragment (2) and a distal bone fragment (4). The implant (12) is secured to the distal bone fragment (4) by the locking device (18). The buttress (16) engages the implant (12) through an opening (30). The reducer (14) contains a compressing screw (24) that applies a force (60) on the buttress (16), reducing the fracture. According to another embodiment of the invention, the reducer (114) contains a cam mechanism (124) which applies a force (186) on the buttress (116), which does not engage the implant (112), that pushes the proximal bone fragment (102) to reduce the fracture. According to another embodiment of the invention, the reducer (214) is a jacking mechanism that pushes the proximal bone fragment (202) while pulling the implant (212) and distal fragment (204) to reduce the fracture.

20 Claims, 8 Drawing Sheets

(56) References Cited

U.S. PATENT DOCUMENTS

| | | | |
|---|---|---|---|
| 4,875,475 A * | 10/1989 | Comte et al. | 606/64 |
| 5,045,708 A | 9/1991 | Cooper | |
| 5,100,404 A | 3/1992 | Hayes | |
| 5,247,182 A | 9/1993 | Servant et al. | |
| 5,352,228 A * | 10/1994 | Kummer et al. | 606/64 |
| 5,429,640 A | 7/1995 | Shuler et al. | |
| 5,665,086 A | 9/1997 | Itoman et al. | |
| 6,579,294 B2 | 6/2003 | Robioneck | |
| 6,648,891 B2 * | 11/2003 | Kim | 606/86 B |
| 6,652,528 B2 | 11/2003 | Vandewalle | |
| 2003/0069581 A1 | 4/2003 | Stinson et al. | |
| 2003/0114855 A1 * | 6/2003 | Wahl et al. | 606/67 |
| 2003/0236529 A1 * | 12/2003 | Shluzas et al. | 606/105 |
| 2004/0172026 A1 * | 9/2004 | Ekholm et al. | 606/62 |
| 2004/0215204 A1 | 10/2004 | Davison et al. | |
| 2005/0096656 A1 * | 5/2005 | Behrens | 606/64 |
| 2006/0129247 A1 * | 6/2006 | Brown et al. | 623/23.46 |
| 2006/0251219 A1 | 11/2006 | Cadwalader et al. | |
| 2008/0058813 A1 * | 3/2008 | Gotfried | 606/62 |
| 2009/0149861 A1 | 6/2009 | Brodsky et al. | |

FOREIGN PATENT DOCUMENTS

| | | |
|---|---|---|
| DE | 29712294 U1 | 11/1997 |
| EP | 0073455 | 3/1983 |
| EP | 0073455 A2 | 3/1983 |
| EP | 1304082 | 4/2003 |
| EP | 1304082 A | 4/2003 |
| EP | 1350479 | 10/2003 |
| EP | 1350479 A | 10/2003 |
| WO | WO 2007/038238 A | 4/2007 |

OTHER PUBLICATIONS

International Preliminary Report on Patentability; PCT/US2007/002257; Jul. 29, 2008; 9 pages.

First Examination Report; European Patent Office; European Patent Application No. 07762754.5; Feb. 25, 2013; 4 pages.

Second Examination Report; European Patent Office; European Patent Application No. 07762754.5; Jun. 25, 2013; 9 pages.

* cited by examiner

ASSEMBLIES FOR THE REDUCTION OF A FRACTURE

RELATED APPLICATION

This application is a National Stage of International Application No. PCT/US2007/002257, filed Jan. 26, 2007, which claims the benefit of U.S. Provisional Patent Application Ser. No. 60/762,988, entitled "Implant and Instrument for the Reduction of a Fracture" and filed on Jan. 27, 2006. Each prior application is incorporated by reference in its entirety as though fully disclosed herein.

RELATED FIELDS

Embodiments of the present invention are directed to reducing skeletal fractures using various implants and/or instrumentation.

BACKGROUND

Fractures across long bones, such as the femur or tibia, as well as fractures of other bones, such as the humerus or bones in the ankle/hind foot region, are fairly common. These fractures may result in two or more portions of bone that need to be compressed and held together during the healing process. Fracture fixation of such portions can be challenging because of the difficulty of properly aligning and then securing fractured bone segments in place to allow the bone to heal. The bone fragments may be secured using a bone plate or an intramedullary nail (with or without compression) or using other implants and/or instrumentation.

Whether fixation uses an intramedullary nail, bone plate, or other types of implants, the reduction of the segments of a long bone fracture may be a critical aspect of fracture fixation. Reduction can be important to ensure that the bone will heal properly and more quickly, to decrease pain and prevent deformity, and to allow the patient to regain use of the bone and limb. When intramedullary nails or bone plates are implanted to treat fractures, there is a need to reduce a fracture with a high level of control and accuracy. Additionally, it may be desirable to reduce the fracture using a minimally invasive procedure. Finally, it may also be important to leave the two portions of the bone in a compressed state to ensure proper and quick healing.

Typically, when an implant, such as an intramedullary nail or bone plate, is used, the surgeon will position the implant so that the implant traverses or extends across the fracture between the two portions of the bone. Once this is done, the surgeon will typically lock one end of the implant to a bone portion.

After fixing one of the ends of the implant to one of the bone fragments, it may be desirable to reduce the fracture. One known method for reducing the fracture is for the surgeon to "back-slap" a drill guide attached to the implant. While reduction may occur, this method is not optimal. First, a "back-slap" is not a controlled reduction. Second, there is no instrument used to hold the compression between the two portions of the fragmented bone while the proximal end of the implant is locked to the other bone portion, which may lead to locking the bone fragments in a non-compressed state.

Another known method of reducing a fracture is by using an implant with a slot. Once the implant is settled in the correct position of the fracture, a bone screw is inserted and locked into the slot. The fracture is reduced when a compression screw pushes against the locked bone screw, thereby pushing on the implant itself. While this method does allow for control and holds the compression while the other end of the implant is locked, this method brings about other problems. First, the method requires pre-assembly, which constrains the surgeon to plan to use the compression feature before implanting the implant. Second, a load is placed on the bone screw which can cause the screw to flex. Leaving the bone screw in such a post-op state may lead to the screw becoming deformed. Also, this assembly prevents additional screws from being placed in an optimal region of the upper fracture due to the compression screw and slot size occupying the same area on the implant and fracture.

Accordingly, it may be desirable to provide instrumentation and implants that allow for efficient, controlled, and accurate reduction of a fracture. It may also be desirable for such a device that does not leave the implant and its components in a state of stress after the fracture has been reduced and the implant locked in place. Further, it may be desirable for the implant and its instrumentation to allow other locking screws to be placed in optimal regions while holding the fracture in a compressed state.

SUMMARY

Embodiments of the present invention may include a fracture reducing assembly that includes a fracture reducing instrument and an implant. The fracture reducing instrument may include a reducer that interacts with a buttress engaged with one of the bone fragments such that the interaction of the reducer with the buttress facilitates the reduction of the fracture in a controlled manner. Such fracture reducing assemblies may allow fixation of the two bone fragments with respect to the implant while the fracture remains in a compressed state without compromising the structure integrity of the implant and the implant's associated components (such as fixation devices). After fixation, the fracture reducing instrument may be disassociated from the implant. A controlled fracture reducing instrument may include a reducer that applies a controlled force to one bone fragment, directly or indirectly, while keeping the implant locked in position relative to the other bone fragment. The controlled fracture reducing instrument may be removed after both fragments are locked in place with the implant. In some embodiments of the present invention, the assembly may also allow for multiple locking devices in an optimal region of the implant while maintaining the bone fragments in a state of compression. In some embodiments, the assembly may reduce the fracture without the need of a buttress.

According to an aspect of the present invention there may be provided an assembly for the reduction of a first bone fragment with respect to a second bone fragment, the assembly comprising an implant, a first locking device for locking the first bone fragment to the implant, a buttress adapted to be rigidly mounted to the second bone fragment in a removable manner, and a removable reducer for associating with the implant, wherein actuation of the reducer exerts a force on the buttress to reduce the fracture.

According to some embodiments of the present invention, the implant may include a first opening and the buttress may be adapted to extend through the first opening.

According to some embodiments of the present invention, the reducer may include a compression screw and an attachment bolt, the attachment bolt may include an internally threaded surface for engaging an externally threaded surface of the compression screw and an externally threaded surface for engaging an internally threaded surface of the implant.

According to some embodiments of the present invention, the attachment bolt may be adapted to attach a jig to the implant, the jig may be adapted to at least partially engage the buttress and may be able to guide the buttress through the first opening of the implant.

According to some embodiments of the present invention, the implant may have at least one locking hole located in a separate plane from the first opening and may be able to receive a second locking device.

According to some embodiments of the present invention, the first opening may be an elongated slot.

According to some embodiments of the present invention, the buttress may be a drill, peg, or pin or combinations thereof.

According to some embodiments of the present invention, the buttress may not be able to intersect the implant.

According to some embodiments of the present invention, the reducer may include a cam mechanism.

According to some embodiments of the present invention, the assembly may include a jig, the jig may be able to be attached to the implant through an attachment bolt and the cam mechanism may be adapted to be attached to the jig.

According to some embodiments of the present invention, the buttress may be adapted to engage the cam mechanism.

According to some embodiments of the present invention, the buttress may be one or more drills, pegs, or pins or combinations thereof.

According to some embodiments of the present invention, the assembly may include a second locking device and the implant may include a second opening where the second locking device may be adapted to lock the second bone fragment to the implant through the second opening.

According to some embodiments of the present invention, the implant may be a nail or a bone plate.

According to some embodiments of the present invention the first locking device may be a bone screw.

According to an aspect of the present invention there may be provided an assembly for the reduction of a first bone fragment with respect to a second bone fragment, the assembly may include an implant, a first locking device for locking the first bone fragment to the implant, and a jacking mechanism for associating with the implant, such that actuation of the jacking mechanism may exert a force in a first direction against the second bone fragment and a second force on the implant to reduce the fracture.

According to some embodiments of the present invention, the implant may be a nail.

According to some embodiments of the present invention, the first locking device may be a bone screw.

According to some embodiments of the present invention, the assembly may also include a jig, the jig may be attached to the implant through an attachment bolt.

According to some embodiments of the present invention, the assembly may also include a second locking device, the second locking device for locking the second bone fragment to the implant.

Other and alternate features, aspects, and advantages of various embodiments of the present invention, as well as the structure and operation of various embodiments of the present invention, are described in detail below with reference to the accompanying drawings. Moreover, "embodiment" as used herein can be considered to mean an "aspect" of the invention, and vice versa.

DETAILED DESCRIPTION OF THE INVENTION

Figure 1:
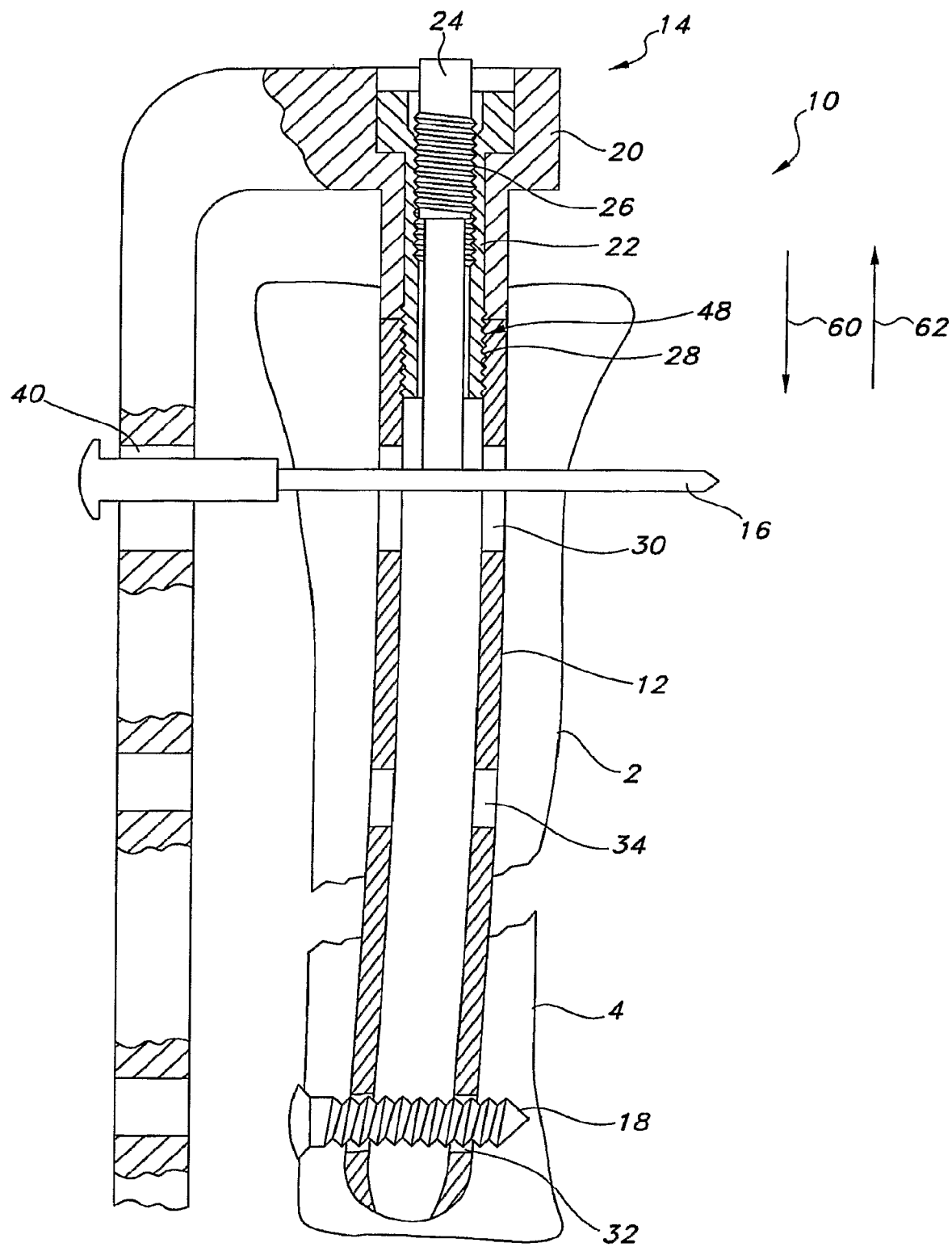
FIG. 1 shows, in partial cross-section, an implant and instrument assembly according to one embodiment of the present invention.
Figure 2:
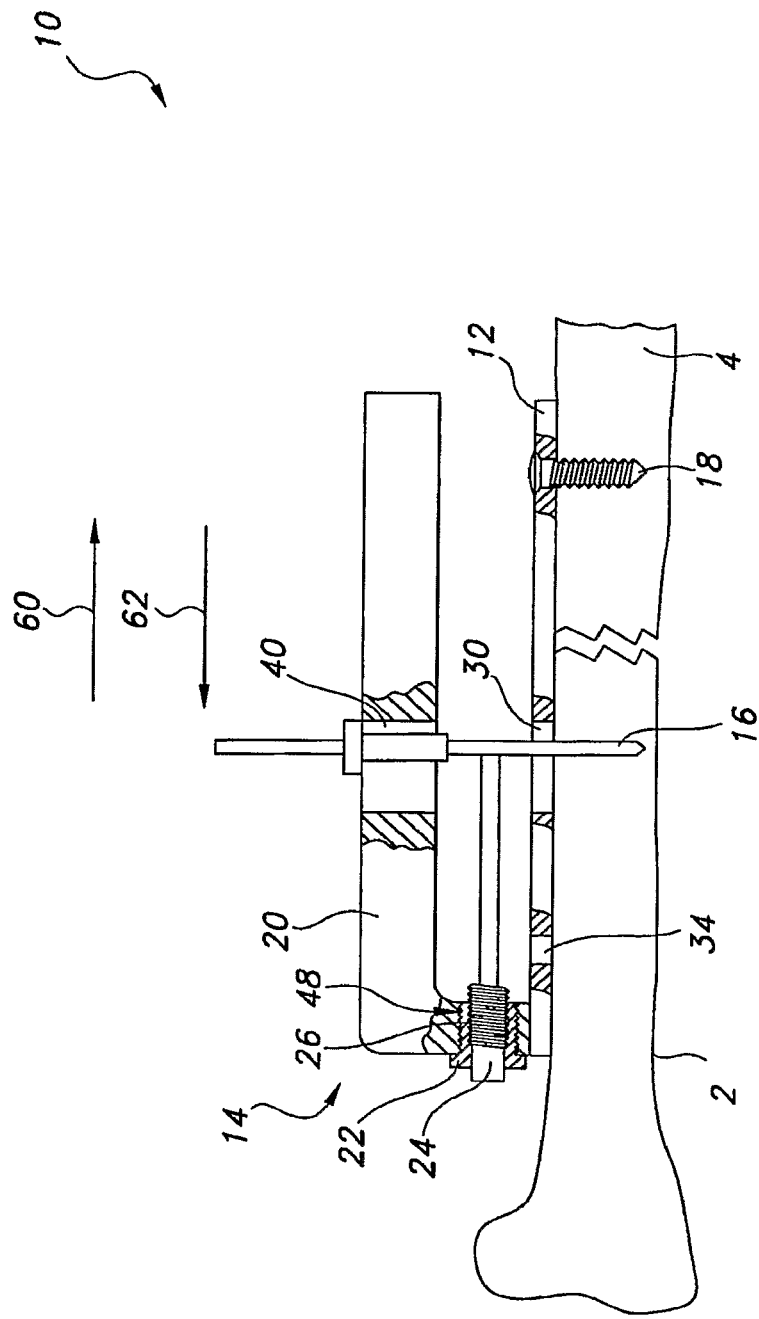
FIG. 2 shows, in partial cross-section, a bone plate assembly according to another embodiment of the present invention.
Figure 3:
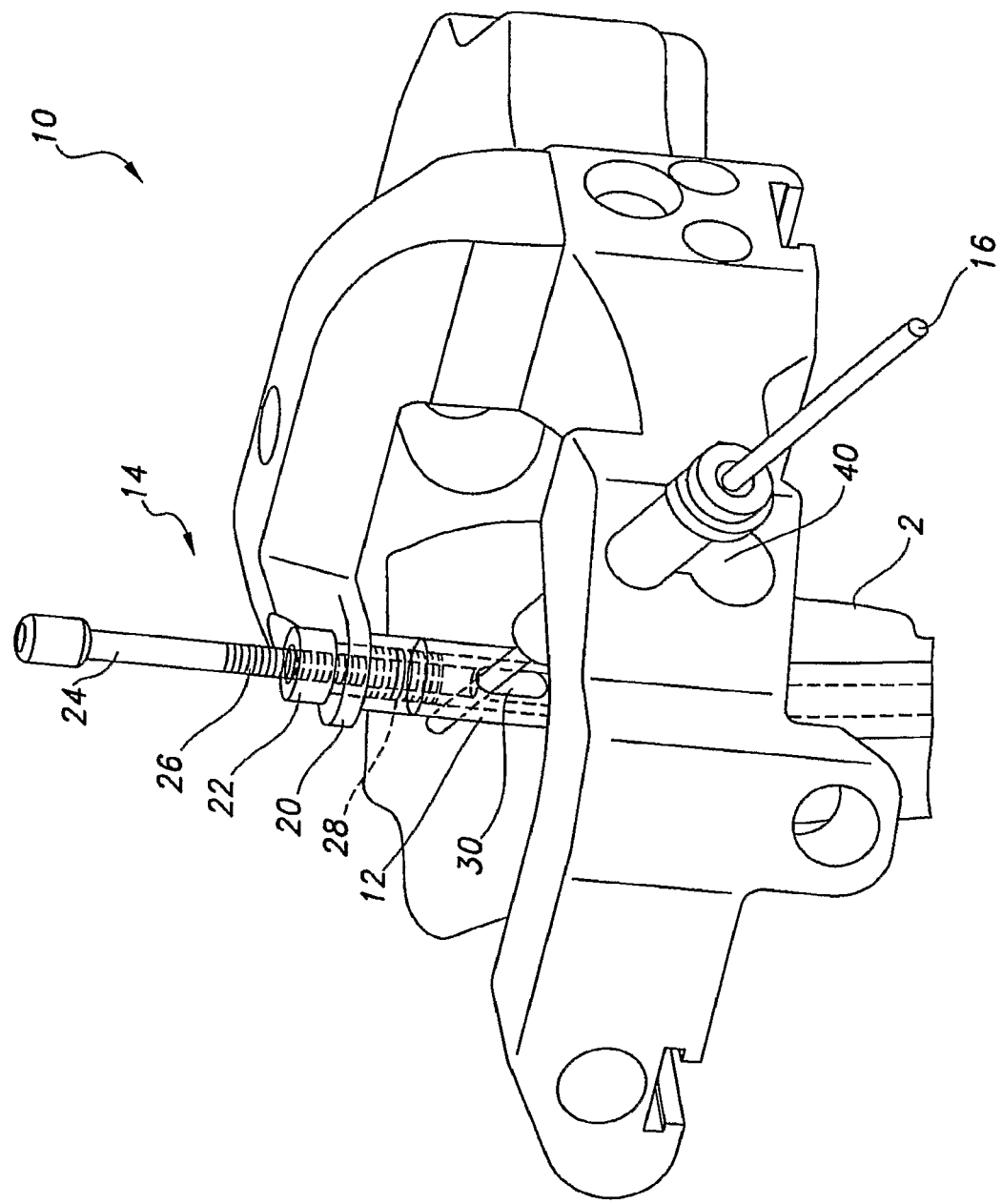
FIG. 3 shows a portion of an intramedullary nail assembly according to another embodiment of the present invention.

FIGS. 1-4 illustrate a controlled fracture reducing assembly 10 according to some embodiments of the present invention. FIG. 1 shows the assembly 10 that includes an implant 12, a reducer 14, a buttress 16, and a locking device 18. The controlled fracture reducing assembly 10 may be used to reduce two or more bone fragments 2, 4. In the embodiment shown in FIGS. 1 and 3-4, the implant 12 is a intramedullary nail. However, the implant of the present invention is not limited to nails; as illustrated in FIG. 2, other types of implants including, but not limited to bone plates may be used instead of or in addition to an intramedullary nail. The implant 12 shown in FIG. 1 includes a first opening 30 through which the buttress 16 passes. As shown in FIG. 1, the first opening 30 may be an elongated slot. However, in other embodiments, the first opening 30 is not an elongated slot and may be any opening that allows at least some longitudinal movement of buttress 16 with respect to implant 12. FIG. 1 shows a second opening 32 positioned at the distal end of implant 12, which locking device 18 may pass through to distally lock implant 12 to bone fragment 4. The locking device 18 shown in FIG. 1 is a bone screw, but other locking devices, including, but not limited to, a pin or other similar structure, may be used.

The implant 12 may include additional openings, such as third opening 34 shown in FIGS. 1-2 and 4-5, which may allow for additional locking devices to be used to secure the proximal bone fragment 2 to the implant 12 once the fracture has been reduced. In other embodiments, third opening 34 is unnecessary and first opening 30 may be used to lock the implant 12 to proximal bone fragment 2. In still other embodiments, proximal locking is not necessary.

Figure 4:
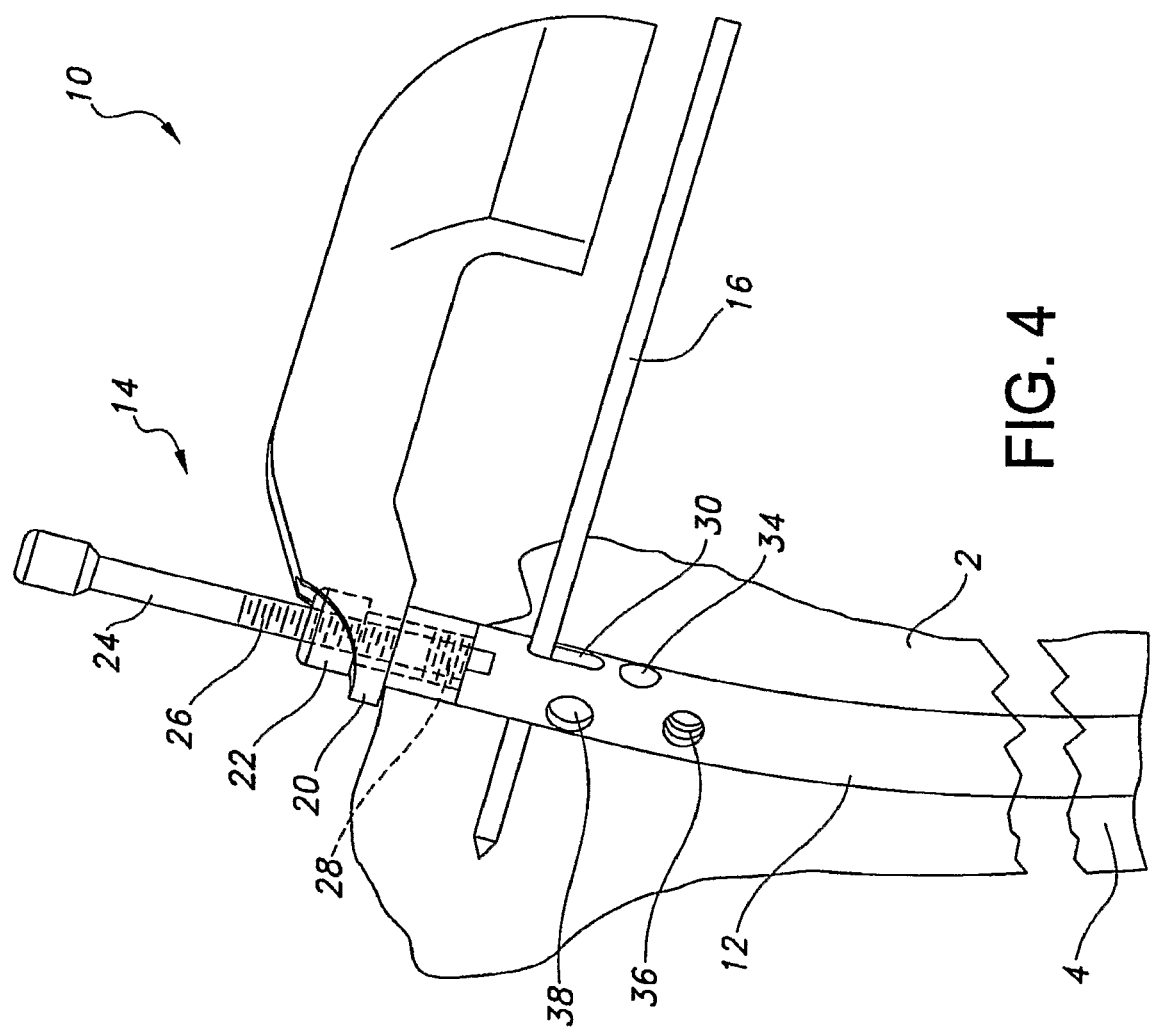
FIG. 4 shows a cut-away view of the assembly of FIG. 3.
Figure 5:
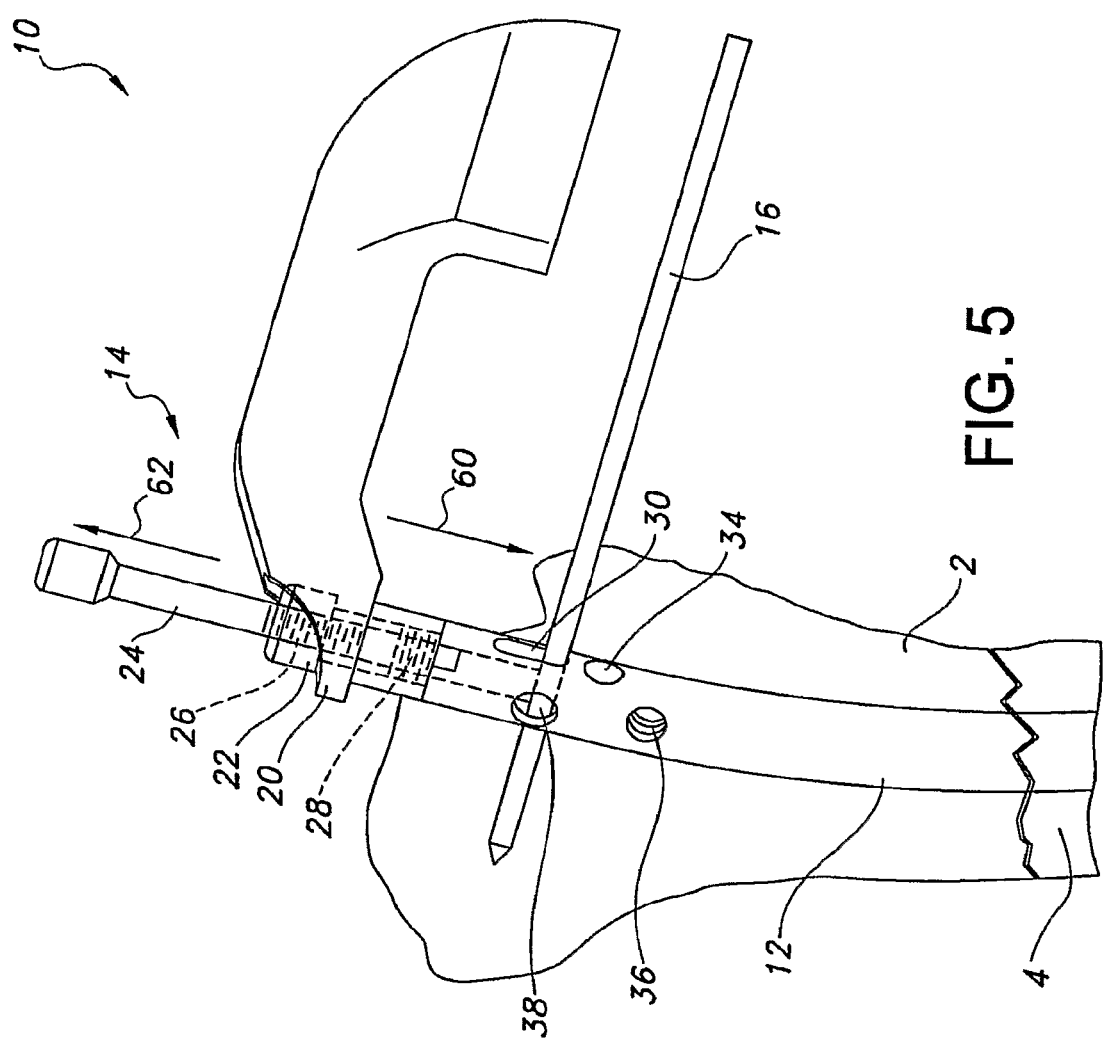
FIG. 5 shows another cut-away view of the assembly of FIG. 3.

As shown in FIGS. 4-5, proximal portions of implant 12 may include a first and a second locking openings 36 and 38 that extend through the implant 12 in different directions than first opening 30 and third opening 34. The first and second locking openings 36 and 38 may receive additional locking devices. The first and second locking openings 36 and 38, or other additional openings, may increase the number of locking options available to the surgeon. Additionally, with the first opening 30 and third opening 34 and the first and second locking openings 36 and 38 being located in the proximal end of the implant, fractures located closer to the proximal end of the implant 12 may be reduced.

In the embodiment of FIG. 1, the reducer 14 shown includes a jig 20, an attachment bolt 22, and a compression screw 24. The jig 20 has a guide opening 40, which may guide a drill when drilling holes in the proximal bone fragment 2 to ensure alignment with the first opening 30. The jig 20 may also include other guide openings for guiding drilling for other openings in implant 12. Guide opening 40 may be used to guide the buttress 16 to engage the proximal bone fracture 2 and to extend through implant 12 through first opening 30.

The attachment bolt 22 shown in FIG. 1 allows the jig 20 to be attached to a proximal portion of the implant 12 using the attachment bolt's threaded external surface 28 to engage an internally threaded surface 48 of the implant 12. The attachment bolt 22 is cannulated and includes a threaded interior surface 26, which allows compression screw 24 to pass through and engage attachment bolt 22 such that rotation of compression screw 24 lowers or raises the compression screw, depending on the direction of rotation.

The buttress 16 shown in FIGS. 1-5 is a drill bit. However, in other embodiments of the present invention, other structures may be used as a buttress, including, but not limited to, a pin, a peg, or the like.

FIG. 2 shows another embodiment of the fracture reducing assembly. The implant 12 of the assembly 10 shown in FIG. 2 is a bone plate. The reducer 14 is made up of the jig 20, the attachment bolt 22, and the compression screw 24. The jig 20 attaches to the bone plate 12, and may provide a guide opening 40 for the inserting of the buttress 16 through the first opening 30. The bone plate 12 is locked to distal bone fragment 4 with the assistance of the locking device 18 through second opening 32. The compression screw 24 may pass through and engage the attachment bolt 22 such that rotation of compression screw 24 lowers or raises the compression screw, depending on the direction of rotation. However, in other embodiments, there is no need for an attachment bolt 22, and there fore the compression screw 24 engages a threaded interior surface of a guide hole of the jig 20. Lastly, third opening 34 allows the bone plate 12 to be locked to the proximal bone fragment 2 upon reduction of the fraction.

The fracture reducing assembly embodiments shown in FIGS. 1-5 may be used to reduce bone fractures, such as the fractures illustrated in FIGS. 1 and 2. In some embodiments, it may be necessary to first prepare the bone to receive the implant. For example, if the implant is a nail, the canal of the fractured bone may be reamed. Also, the fractured portions of the bone might need to be aligned with one another. After the bone has been prepared to receive the implant 12, the implant 12 may be coupled with the jig 20 through the attachment bolt 22. The jig 20 may also be attached after the implant 12 has been inserted, but in most cases, the jig 20 is attached before insertion. Either way, the implant 12 may be installed to extend across or traverse the fracture. Next, the implant 12 may then be locked to the distal bone fragment 4 with the locking device 18 through the second opening 32 located at the distal end of the implant 12. In some instances, the distal bone fragment 4 is prepared to receive the locking device 18 by drilling a hole through the bone in alignment with second opening 32. However, the locking device 18 may be inserted without preparing a hole.

Once the distal fragment bone 4 is locked to the implant 12, the proximal bone fragment 2 may be prepared to receive the buttress 16. A drill bit may be inserted through the guide opening 40 to drill through one side of the proximal bone fragment 2, extend through the proximal end of the implant's first opening 30, and into the other side of the proximal bone fragment 2. To ensure that the buttress 16 extends through the upper portion of the implant's first opening 30, a drill sleeve may be used. If a drill sleeve is used, once the hole is prepared, the drill sleeve is removed, so that the buttress 16 may translate the guide opening 40 as the buttress 16 would along the implant's first opening 30. In this embodiment of the present invention, the drill bit may be used as the buttress 16. However, in other embodiments, the drill bit may be removed and another device, such as a pin, or a peg, or the like may be used.

In the embodiments shown in FIGS. 1-5, once the buttress 16 is rigidly secured, the compression screw 24 may be inserted through the attachment bolt 22. The compression screw 24 may then be rotated until the compression screw 24 contacts the buttress 16, as shown in FIG. 1. At this point, rotating the compression screw 24 further will result in a downward force 60 being applied to the buttress 16 and a corresponding upward force 62 being applied to implant 12. Because the buttress 16 is anchored in the proximal bone fragment 2 and the compression screw 24 is engaged with the attachment bolt 22, the proximal bone fragment 2 moves toward the distal bone fragment 4, reducing the fracture.

In some embodiments, once reduction of the fracture has been achieved, the implant 12 may be locked to the proximal bone fragment 2. While the compression screw 24 still engages the buttress 16, as shown in FIG. 5, additional locking devices, similar to locking device 18 used to secure the distal bone fragment 4, may be used to secure the proximal bone fragment 2 to the implant 12 through third opening 34. Once the proximal bone fragment has been locked to the implant 12, keeping the fracture in a compressed state, the compression screw 24 may disengage the buttress 16. The buttress 16 and the compression screw 24 may be removed. After this occurs, other locking devices similar to locking device 18 may be used to lock the implant 12 through the first and second locking openings 36 and 38 to the proximal bone fragment 2.

The preceding was a description of one method of using the fracture reducing assemblies depicted in FIGS. 1-5. Other methodologies are also possible, and within the scope of the present invention.

Figure 6:
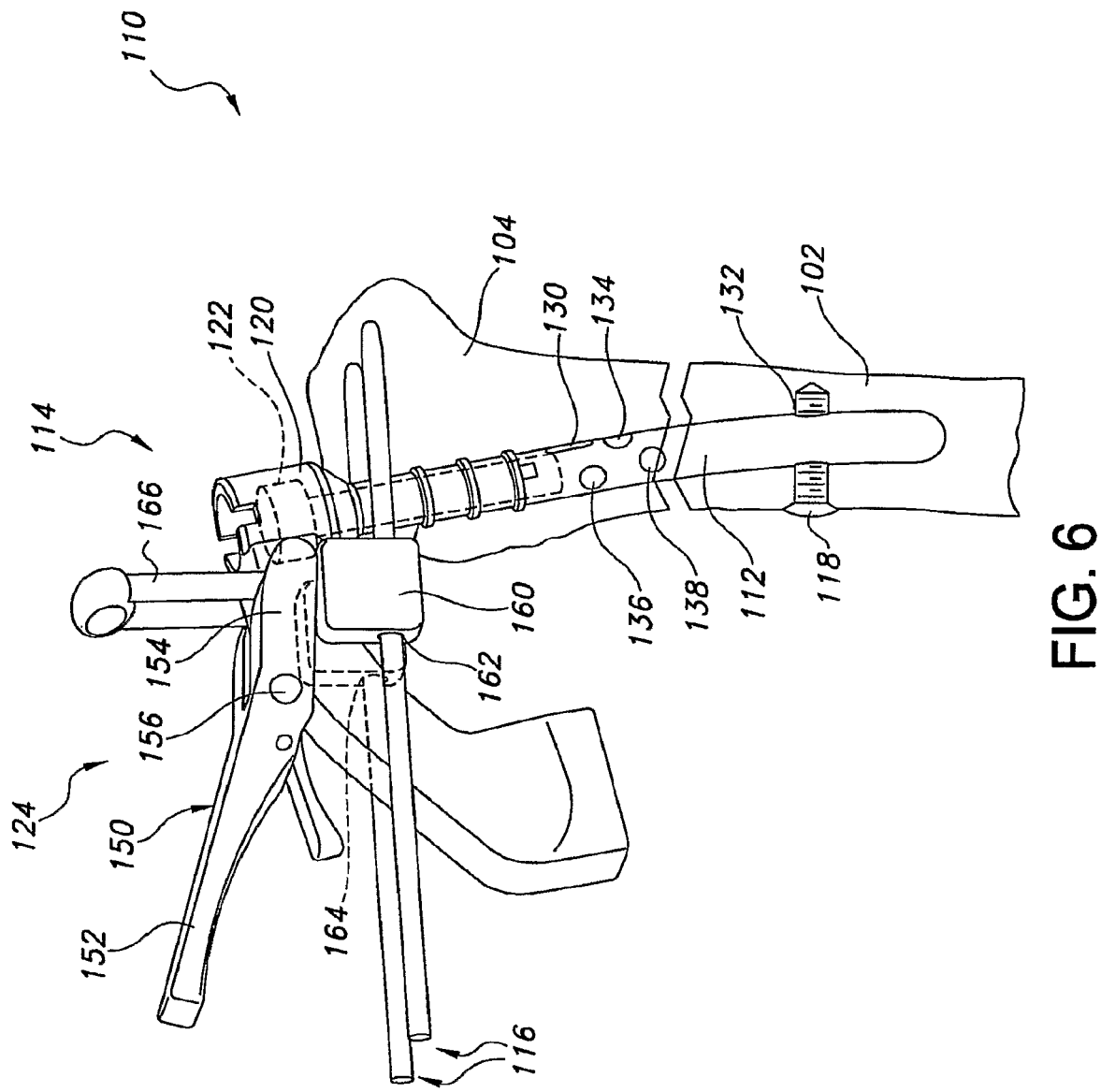
FIG. 6 shows an intramedullary nail and instrument assembly in accordance with another embodiment of the present invention.

FIG. 6 shows another embodiment of the present invention that utilizes similar mechanisms as those described above to reduce a fracture. This alternative controlled fracture-reducing device 110 includes an implant 112, a reducer 114, a buttress 116, and a locking device 118. As shown in FIG. 6, the implant 112 is an intramedullary nail. However, the implant 112 is not limited to nails, as those skilled in the art would understand that other implants, such as a bone plate, which are capable of providing support to a fractured bone, may be used.

The reducer 114 shown in FIG. 6 includes a jig 120, an attachment bolt 122, and a cam mechanism 124. Similar to the embodiments shown in FIGS. 1-5, the jig 120 may be coupled to the implant 112 through the attachment bolt 122. The cam mechanism 124 may be attached to the jig 120. The cam mechanism 124 may include a cam 150 rotatably associated with a pair of blocks 160, which are slidably associated with jig 120. The cam 150 has an extending arm 152 and a lobe 154. The cam 150 rotates around the pin 156. The cam mechanism 124 may be connected to the jig 120 through slots on the jig 120 and protrusions located on the cam mechanism 124 while the blocks 160 of the system 124 are connected to the jig 120 through a sliding track system 166. The blocks 160 have a first and second block openings 162 and 164, through which buttresses 116 may pass, such that rotating arm 152 in the clockwise direction 184 shown in FIG. 7 causes lobe 154 to apply a downward force 186 to blocks 160.

Figure 7:
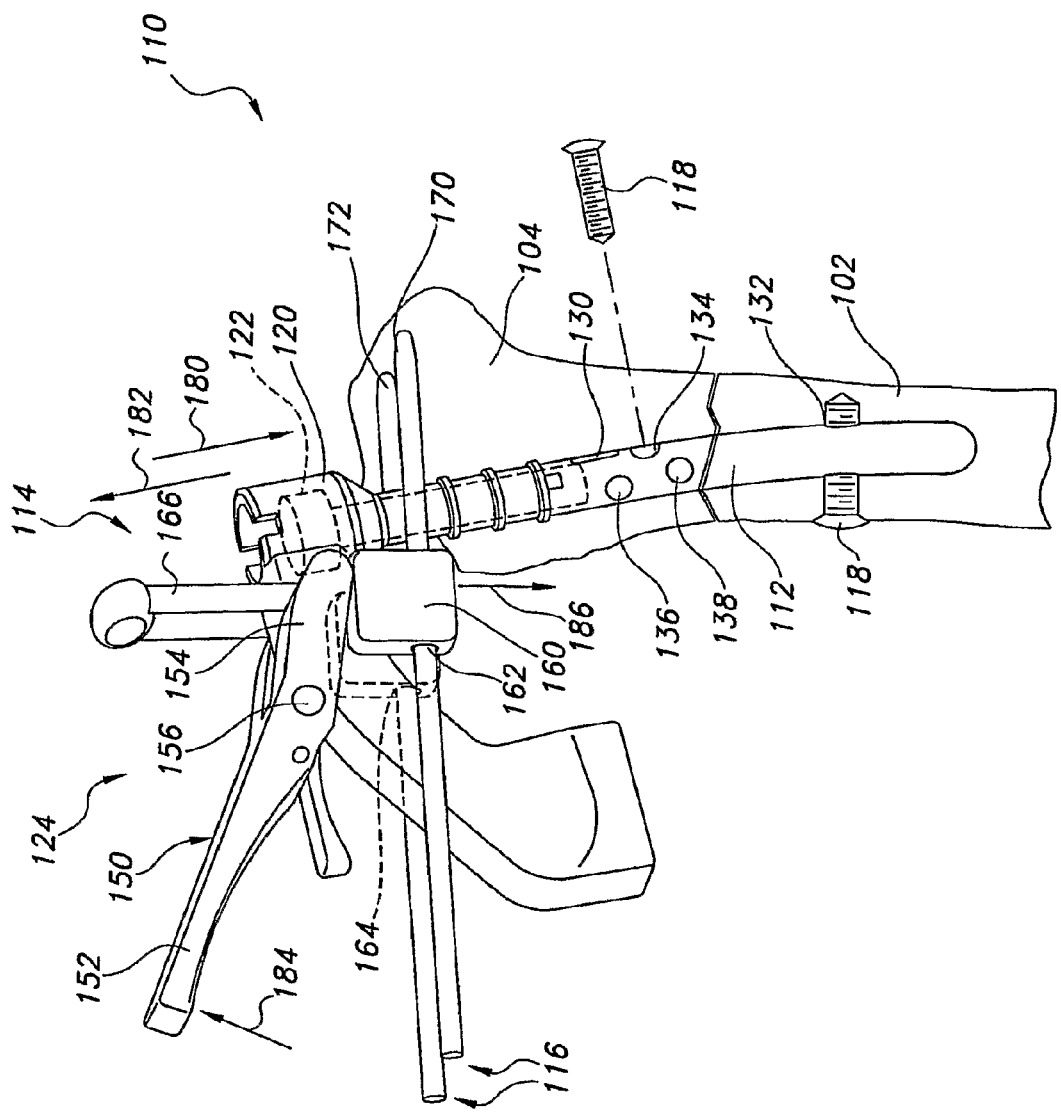
FIG. 7 shows another view of the assembly shown in FIG. 6.

The fracture reducing assembly embodiment shown in FIGS. 6-7 may be used to reduce bone fractures. In some embodiments, it may be necessary to first prepare the bone to receive the implant 112. The bone fragments may need to be realigned with one another and, in the case of using an intramedullary nail, the canal of the bone fragments may be reamed. Once the fracture has been prepared to receive the implant 112, the implant 112 may be coupled with the jig 120 through the attachment bolt 122. The jig 120 may also be attached after the implant 112 has been inserted, but in most cases, the jig 120 is attached before insertion. Either way, when the implant 112 is ready to be installed, the implant 112 is implanted to traverse the fracture. Once the fracture has been traversed by the implant 112, the distal bone fragment 104 may be prepared to be locked to the implant 112. In some instances, a hole is drilled in the fragment 104 that extends through the distal opening 132 of the implant 112 before the locking device 118 is used. However, the locking device 118 may be inserted without preparing a hole.

After the distal bone fragment 104 is locked to implant 112, the cam mechanism 124 may be attached to the jig 120. Once attached, the cam mechanism 124 may be set in a position in which the lobe 154 does not engage the blocks 160. When the blocks are in this position, the first and second block openings 162 and 164 may serve as guides for drilling anchoring holes in the proximal bone fragment 102. When the drilling occurs, at no time does the drill extend through the implant 112; the holes run through the proximal bone fragment 102 along either side of the implant 112. With the drill holes provided, the buttresses 116 may be inserted through first and second block openings 162 and 164 and into the bone. In some embodiments, the drill bits used to drill the holes may be left in the drilled holes and first and second block openings 162 and 164 to serve as the buttresses 116. In other embodiments, the drill bits may be removed and other items, such as, but not limited to, pins and pegs, or the like may be used.

Once the buttress 116 is rigidly secured, the extended arm 152 is activated through the application of a force 184, the lobe 154 applies a downward force 186 upon the blocks 160. Because the implant 112 is attached to the jig 120, which is attached to the cam 150, the only portion of the device 110 that is free to move are the blocks 160 that are engaged by the buttresses 116 through first and second block openings 162 and 164. As such, a force 180 that is applied to the buttresses 116 is applied to the proximal bone fragment 102, which moves the proximal bone fragment 102 along the implant 112 towards the distal bone fragment 104, and a corresponding upward force 182 is applied to the implant 112. Because the buttress 116 is anchored in the proximal bone fragment 102 and the blocks 160 of the cam mechanism 124, which is attached to the jig 120 attached to the implant 112, the proximal bone fragment 102 moves towards the distal bone fragment 104, reducing the fracture.

In some embodiments, once reduction of the fracture has been achieved, the implant 112 may be locked to the proximal bone fragment 102. While the lobe 154 is still engaging the blocks 160, which in turn continue to apply the force 180 on the buttresses 116, keeping the fracture in a state of compression, additional locking devices 118 may be used to secure the proximal bone fragment 102 to the implant 112 through openings 130 and 134 and locking openings 136 and 138. However, in some embodiments, the proximal bone fragment 102 may not need to be locked to the implant 112. In either case, once the fracture is secured, the buttresses 116 and the cam mechanism 124 may be removed.

The preceding was a description of one method of using the fracture reducing assemblies depicted in FIGS. 6-7. Other methodologies are also possible, and within the scope of the present invention.

Figure 8:
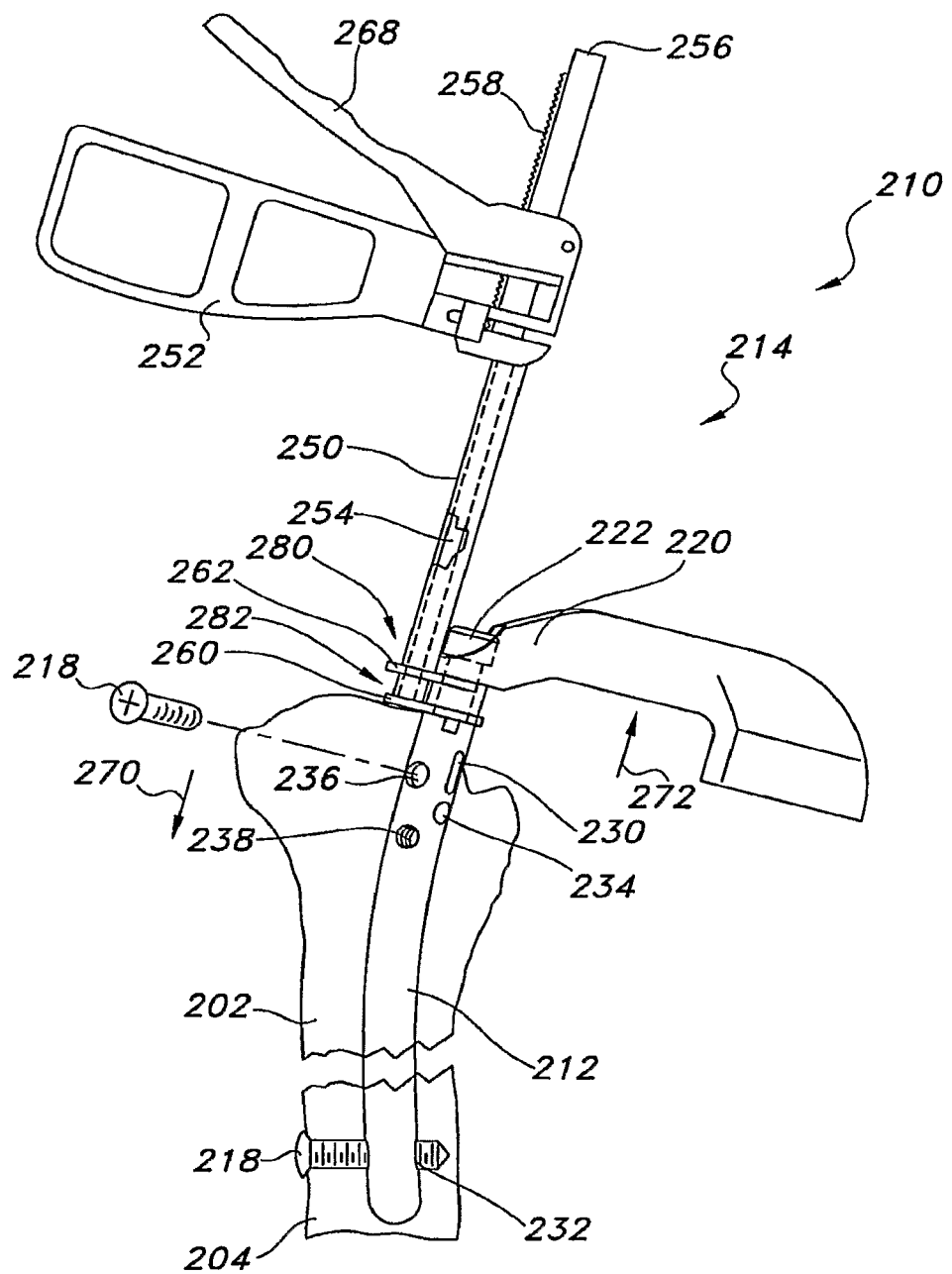
FIG. 8 shows an intramedullary nail and instrument assembly according to another embodiment of the present invention.

FIG. 8 shows another embodiment of the present invention in which the fracture reduction assembly 210 includes a jacking mechanism 214. The assembly 210 includes an implant 212, the jacking mechanism 214, a locking device 218, and a jig 220. The jig 220 may be attached to the implant with an attachment bolt 222. The implant 212 may be locked to the distal bone fragment 204 through the use of a locking device 218 similar to other locking devices discussed above through the implant's 212 distal opening 232.

The jacking mechanism 214 may include a static rod 250 that is connected a handle 252. At the distal portion 280 of the static rod 250, there may be a coupling 262 that is used to surround the implant 212 underneath the jig 220. There is also a moving rod 254, which may have a ratcheted surface 258 along a proximal portion 256. The moving rod 254 may also have a coupling 260 attached at the distal portion 282 that surrounds the implant 212 underneath the jig 220. Both couplings 260 and 262 may have a cut out portion that matches the diameter of the implant 112, which ensures a good fit. The moving rod 254 may be contained partially within the static rod 250. Attached to the handle 252 is a ratcheting handle 268. The ratcheting handle 268 engages the ratcheted surface 258 of the proximal end 256 of the moving rod 254, moving the rod 254 in a distal direction.

The fracture reducing assembly 210 embodiment show in FIG. 8 may be used to reduce bone fractures. In some embodiments, it may be necessary to prepare the bone to receive the implant 212. As described above, the fracture may need to be realigned and the canal of the bone reamed. After the bone has been prepared to receive the implant 212, the implant 212 may be coupled with the jig 20 through the use of the attachment bolt 222. The jig 220 may also be attached after the implant has been inserted, but in most cases, the jig 220 is attached before insertion. The implant 212 in either case may then be inserted, traversing the fracture. Once the implant 212 has been installed to traverse the fracture, the implant 212 may then be locked to the distal bone fragment 204 with locking device 218 through the distal opening 232. In some instances, the distal bone fragment 204 may be prepared to receive the locking device 218 by having a hole that extends through the distal opening 232 drilled. However, the locking device 218 may be inserted through the distal opening 232 without preparing a hole first.

Once the distal bone fragment 204 is locked to the implant 212, the jacking mechanism 214 may be connected to the implant 212 and the jig 220. The coupling 260 connected to the moving rod 254 and the coupling connected to the static rod 250 may be placed around the implant 212 and underneath the jig 220.

Once every thing is in place, the ratcheting handle 268 may be activated. The ratcheting handle 268 engages the ratcheted surface 258 of the moving rod 254, pushing the rod 254 downward. While the moving rod 254 moves in an distal direction, the attached coupling 260 engages the proximal bone fragment 202 and applies a downward force 270 on the fragment 202. As the downward force 270 is applied, a corresponding upward force 272 is applied by the coupling 262 attached to the static rod 250 against the implant 212 and jig 220. This results in the static rod 250 and attached coupling 262 pulling the implant 212 and the locked distal bone fragment 204 upward towards the downwards moving proximal bone fragment 102, thereby reducing the fracture. The ratcheting may continue until the fracture is reduced and is in a state of compression. At completion, the proximal bone fragment 202 may be locked with a locking device 218 through locking openings 236 and 238, and openings 230 and 234. Once the proximal fragment 202 is locked to the implant 212, the jacking mechanism 214 may be removed, as well as the jig 220.

The preceding was a description of one method of using the fracture reducing assemblies depicted in FIG. 8. Other methodologies are also possible, and within the scope of the present invention.

According to an aspect of the present invention, there may be provided a method for reducing a fracture between a first bone fragment with respect to a second bone fragment, the method including installing an implant to traverse the fracture, locking the first bone fragment to the implant, connecting a reducer to the implant, securing a buttress to the second bone fragment, activating the reducer to reduce the fracture, and removing the reducer and buttress after reduction of the fracture.

According to some embodiments of the present invention, installing the implant to traverse the fracture includes implanting an intramedullary nail in the bone canal of the first and second bone fragments.

According to some embodiments of the present invention, installing an implant to traverse the fracture includes installing a bone plate across the fracture.

According to some embodiments of the present invention, securing the buttress to the second bone fragment includes securing the buttress to the second bone fragment by rigidly inserting the buttress into the second bone fragment and extending the buttress through a first opening in the implant.

According to some embodiments of the present invention, connecting the reducer to the implant includes connecting the reducer that includes a compressing screw and an attachment bolt, the attachment bolt may include an internally threaded surface for engaging an externally threaded surface of the compressing screw and an externally threaded surface for engaging an internally threaded surface of the implant.

According to some embodiments of the present invention, connecting a reducer to the implant includes connecting the reducer that includes an attachment bolt, the attachment bolt may be adapted to attach a jig to the implant, the jig may be adapted to at least partially engage the buttress and may be able to guide the buttress through the first opening in the implant.

According to some embodiments of the present invention, activating the reducer to reduce the fracture includes activating the reducer by rotating the compression screw, the compression screw applying a force on the buttress to move the second bone fragment towards the first bone fragment.

According to some embodiments of the present invention, connecting a reducer to the implant includes connecting a reducer that includes a cam mechanism and a jig, the jig adapted to be attached to the implant through an attachment bolt.

According to some embodiments of the present invention, securing a buttress to the second bone fragment includes securing the buttress to the second bone fragment by rigidly inserting the buttress into the second bone fragment while not intersecting the implant.

According to some embodiments of the present invention, securing a buttress to the second bone fragment includes securing the buttress to the second bone fragment so that the buttress engages the cam mechanism.

According to some embodiments of the present invention, activating the reducer to reduce the fracture includes activating the cam mechanism, applying a force on the buttress, moving the second bone fragment towards the first bone fragment.

According to an aspect of the present invention, there may be provided a method for reducing a fracture between a first bone fragment with respect to a second bone fragment, the method including installing an implant to traverse the fracture, locking the first bone fragment to the implant, connecting a jacking mechanism to the implant, activating the jacking mechanism to reduce the fracture, and removing the jacking mechanism after reduction of the fracture.

According to some embodiments of the present invention, installing the implant to traverse the fracture includes installing the implant with a jig attached, the jig attached through an attachment bolt, the attachment bolt engaging the implant and the jig.

According to some embodiments of the present invention, installing the implant to traverse the fracture includes installing the implant, the implant being an intramedullary nail.

According to some embodiments of the present invention, connecting a jacking mechanism to the implant includes attaching the jacking mechanism so that the jacking mechanism engages the implant and the second bone fragment.

According to some embodiments of the present invention, activating the jacking mechanism to reduce the fracture includes activating the jacking mechanism so that the jacking mechanism exerts a force in a first direction against the second bone fragment and a second force on the implant to reduce the fracture.

According to some embodiments of the present invention, locking the first bone fragment to the implant includes locking the first bone fragment to the implant by using a locking device and inserting the locking device through the implant and the first bone fragment.

According to some embodiments of the present invention, the method for reducing a fracture may include locking the second bone fragment to the implant while keeping the fracture is a state of compression after activating the reducer to reduce the fracture and before removing the reducer and buttress after reduction of the fracture.

According to some embodiments of the present invention, locking the second bone fragment to the implant while keeping the fracture is a state of compression includes locking the second bone fragment by using a second locking device, the second locking device anchored in the second bone fragment and extending through a locking opening in the implant.

As various modifications could be made in the constructions and methods herein described and illustrated without departing from the scope of the invention, it is intended that all matter contained in the foregoing description or shown in the accompanying drawings shall be interpreted as illustrative rather than limiting. For example, the instruments and techniques described herein may be used with either a intramedullary nail, a bone plate, or other types of implants. Thus, the breadth and scope of the present invention should not be limited by any of the above-described exemplary embodiments, but should be defined only in accordance with the following claims appended hereto and their equivalents.

What is claimed is:

1. An assembly for the reduction of a first bone fragment with respect to a second bone fragment, comprising:
   (a) an implant having a longitudinal axis, and having an elongated slotted proximal opening and a distal opening for bridging between the first and second bone fragments;
   (b) a first locking device passing through the distal opening of the implant, the first locking device for locking the first bone fragment to the implant;
   (c) a buttress adapted to be rigidly mounted to the second bone fragment in a removable manner and passing through the elongated slotted proximal opening of the implant;
   (d) a removable reducer and jig for associating with the implant, the jig having an elongated slotted first opening aligning with the elongated slotted proximal opening of the implant and a second opening aligning with the distal opening of the implant, the buttress positioned within each of the elongated slotted proximal opening of the implant and the elongated slotted first opening of the jig wherein actuation of the reducer exerts an axial force along the longitudinal axis of the implant on the buttress to axially translate the buttress along both the elongated slotted proximal opening of the implant and the elongated slotted first opening of the jig to thereby move the second bone fragment towards the first bone fragment to reduce the fracture.

2. The assembly as recited in claim 1, wherein the reducer comprises a compressing screw and an attachment bolt, the attachment bolt further comprising:

(a) an internally threaded surface for engaging an externally threaded surface of the compressing screw;

(b) an externally threaded surface for engaging an internally threaded surface of the implant; and (c) a proximal head engaged with the jig to removably attach the jig to the implant.

3. The assembly as recited in claim 1, wherein the implant has at least one locking hole positioned adjacent the elongated slotted proximal opening between the elongated slotted proximal opening and the distal opening, the at least one locking hole located in a separate plane from the elongated slotted proximal opening and with a second locking device extending through the at least one locking hole for locking the second bone fragment to the implant.

4. The assembly as recited in claim 1, wherein the reducer comprises a cam mechanism.

5. The assembly as recited in claim 4, wherein the jig is attached to the implant through an attachment bolt and the cam mechanism is attached to the jig.

6. The assembly as recited in claim 5, wherein the buttress is adapted to engage the cam mechanism.

7. The assembly as recited in claim 6, wherein the buttress comprises one or more drills, pegs, pins, or screws.

8. The assembly as recited in claim 1, further including a second locking device, wherein the implant further includes a plurality of locking openings positioned proximately adjacent the elongated slotted proximal opening between the elongated slotted proximal opening and the distal opening, the plurality of locking openings extending through the implant in different directions and different angular orientations, the second locking device extending through one of the plurality of locking openings for locking the second bone fragment to the implant.

9. The assembly as recited in claim 8, wherein the jig includes at least one third opening aligned with a corresponding one of the plurality of locking openings in the implant and structured to guide the second locking device into the corresponding one of the plurality of locking openings.

10. The assembly as recited in claim 1, wherein the second opening of the jig is aligned with the distal opening of the implant to guide the first locking device through the distal opening of the implant.

11. The assembly as recited in claim 1, wherein the jig is removably attached to a proximal end portion of the implant by an attachment bolt, and wherein the reducer comprises a compressing screw threadedly engaged with the attachment bolt for threading displacement along the longitudinal axis of the implant to thereby exert the axial force on the buttress.

12. The assembly as recited in claim 11, wherein the attachment bolt includes:

(a) an internally threaded surface threadedly engaged with an externally threaded surface of the compressing screw; and (b) an externally threaded surface threadedly engaged an internally threaded surface of the implant.

13. The assembly as recited in claim 1, wherein the buttress is positioned in both the elongated slotted proximal opening of the implant and the elongated slotted first opening of the jig when the reducer is actuated and engaged with the buttress; and wherein the buttress translates through and is guided along both the elongated slotted proximal opening of the implant and the elongated slotted first opening of the jig during the actuation of the reducer.

14. An assembly for the reduction of a first bone fragment with respect to a second bone fragment, comprising:

(a) an implant having a longitudinal axis and including an elongated slotted proximal opening and a distal opening for bridging between the first and second bone fragments, the implant further including a plurality of locking openings positioned adjacent the elongated slotted proximal opening between the elongated slotted proximal opening and the distal opening, the plurality of locking openings extending through the implant in different directions, wherein the plurality of locking openings extend through a proximal portion of the implant proximately adjacent the elongated slotted proximal opening;

(b) a first locking device passing through the distal opening of the implant for locking the first bone fragment to the implant;

(c) a buttress adapted to be rigidly mounted to the second bone fragment in a removable manner and passing through the elongated slotted proximal opening of the implant;

(d) a reducer movably engaged with the implant and exerting an axial force along the longitudinal axis of the implant on the buttress to axially translate the buttress along the elongated slotted proximal opening for moving the second bone fragment towards the first bone fragment to reduce the fracture; and (e) a second locking device extending through one of the plurality of locking openings for locking the second bone fragment to the implant and fixing the position of the second bone fragment relative to the first bone fragment.

15. The assembly as recited in claim 14, wherein at least one of the plurality of locking openings is located in a separate plane from the elongated slotted proximal opening.

16. The assembly as recited in claim 14, further comprising a jig attached to the implant and having an elongated slotted first opening aligned with the elongated slotted proximal opening of the implant and a second opening aligned with the distal opening of the implant, the buttress positioned within each of the elongated slotted proximal opening of the implant and the elongated slotted first opening of the jig when the reducer is actuated and engaged with the buttress, wherein the buttress axially translates through and is guided along both the elongated slotted proximal opening of the implant and the elongated slotted first opening of the jig during actuation of the reducer.

17. The assembly as recited in claim 14, further comprising a jig attached to the implant and having a first opening aligned with the elongated slotted proximal opening of the implant, a second opening aligned with the distal opening of the implant, and a third opening aligned with at least one of the plurality of locking openings.

18. The assembly as recited in claim 14, wherein the plurality of locking openings extend through the implant at different angular orientations relative to one another and relative to the elongated slotted proximal opening.

19. The assembly as recited in claim 14, wherein the plurality of locking openings each extend through a proximal end of the implant.

20. The assembly as recited in claim 19, wherein the distal opening extends through a distal end of the implant, and wherein the plurality of locking openings extending through the proximal end of the implant are each positioned nearer the elongated slotted proximal opening than the distal opening.

* * * * *